United States Patent [19]

Showell

[11] Patent Number: 5,478,933
[45] Date of Patent: Dec. 26, 1995

[54] BENZODIAZEPINE DERIVATIVES AND THEIR USE AS ANTAGONISTS OF CHOLECYSTOKININ AND/OR GASTRIN RECEPTORS

[75] Inventor: Graham A. Showell, Welwyn Garden City, United Kingdom

[73] Assignee: Merck Sharpe & Dohme Ltd., Hoddesdon, England

[21] Appl. No.: 225,026

[22] Filed: Apr. 8, 1994

[51] Int. Cl.⁶ .......................... A61K 31/55; C07D 243/24
[52] U.S. Cl. .............................................................. 540/509
[58] Field of Search ................................................. 540/509

[56] References Cited

U.S. PATENT DOCUMENTS 5,302,591  4/1994  Fletcher et al. ..................... 514/221

Primary Examiner—Robert T. Bond
Attorney, Agent, or Firm—Robert J. North; Melvin Winokur

[57] ABSTRACT

Disclosed are new benzodiazepine compounds which are useful as cholecystokinin and gastrin receptor antagonists and are useful in the treatment of anxiety, panic and pain.

6 Claims, No Drawings

BENZODIAZEPINE DERIVATIVES AND THEIR USE AS ANTAGONISTS OF CHOLECYSTOKININ AND/OR GASTRIN RECEPTORS

This invention relates to benzodiazepine compounds which are useful as antagonists of cholecystokinin and gastrin receptors.

Cholecystokinins (CCK) and gastrin are structurally related peptides which exist in gastrointestinal tissue and in the central nervous system (see, V. Mutt, *Gastrointestinal Hormones,* G. B. J. Green, Ed., Raven Press, N.Y., p.169 and G. Nission, ibid. p.127).

Cholecystokinins include CCK-33, a neuropeptide of thirty-three amino acids in its originally isolated form (see, Mutt and Jorpes, *Biochem, J.* 125, 678 (1971)), its carboxylterminal octapeptide, CCK-8 (also a naturally-occurring neuropeptide and the minimum fully active sequence), and 39- and 12-amino acid forms. Gastrin occurs in 34-, 17- and 14-amino acid forms, with the minimum active sequence being the C-terminal tetrapeptide, Trp-Met-Asp-Phe-NH$_2$, which is the common structural element shared by both CCK and gastrin.

CCKs are believed to be physiological satiety hormones, thereby possibly playing an important role in appetite regulation (G. P. Smith, *Eating and Its Disorders,* A. J. Stunkard and E. Stellar, Eds, Raven Press, New York, 1984, p. 67), as well as stimulating colonic motility, gall bladder contraction, pancreatic enzyme secretion and inhibiting gastric emptying. They reportedly co-exist with dopamine in certain mid-brain neurons and thus may also play a role in the functioning of dopaminergic systems in the brain, in addition to serving as neurotransmitters in their own right (see A. J. Prange et al., "Peptides in the Central Nervous System", *Ann. Repts. Med. Chem* 17, 31, 33 [1982] and references cited therein; J. A. Williams, *Biomed Res.* 3 107 [1982]; and J. E. Morley, *Life Sci.* 30, 479 [1982]).

The primary role of gastrin, on the other hand, appears to be stimulation of the secretion of water and electrolytes from the stomach and, as such, is involved in control of gastric acid and pepsin secretion. Other physiological effects of gastrin then include increased mucosal blood flow and increased antral motility. Rat studies have shown that gastrin has a positive trophic effect on the gastric mucosa, as evidenced by increased DNA, RNA and protein synthesis.

There are at least two subtypes of cholescystokinin receptors termed CCK-A and CCK-B (T. H. Moran et al., "Two brain cholecystokinin receptors: implications for behavoural actions", *Brain Res.,* 362, 175–79 [1986]). Both subtypes are found both in the periphery and in the central nervous system.

CCK and gastrin receptor antagonists have been disclosed for preventing and treating CCK-related and/or gastrin related disorders of the gastrointestinal (GI) and central nervous (CNS) systems of animals, especially mammals, and more especially those of humans. Just as there is some overlap in the biological activities of CCK and gastrin, antagonists also tend to have affinity for both CCK-B receptors and gastrin receptors. Other antagonists have activity at the CCK-A subtype.

Selective CCK antagonists are themselves useful in treating CCK-related disorders of appetite regulatory systems of animals as well as in potentiating and prolonging opiate-mediated analgesia [see P. L. Faris et al., *Science* 226, 1215 (1984)], thus having utility in the treatment of pain. CCK-B and CCK-A antagonists have also been shown to have a direct analgesic effect [M. F. O'Neill et al., *Brain Research,* 534 287 (1990)]. Selective CCK and gastrin antagonists are useful in the modulation of behaviour mediated by dopaminergic and serotonergic neuronal systems and thus have utility in the treatment of schizophrenia and depression (Rasmussen et. al., 1991, *Eur. J, Pharmacol.,* 209, 135–138; Woodruff et. al., 1991, *Neuropeptides,* 19, 45–46; Cervo et. al., 1988, *Eur. J. Pharmacol.,* 158, 53–59), as a palliative for gastrointestinal neoplasms, and in the treatment and prevention of gastrin-related disorders of the gastrointestinal system in humans and animals, such as peptic ulcers, Zollinger-Ellison syndrome, antral G cell hyperplasia and other conditions in which reduced gastrin activity is of therapeutic value, see e.g. U.S. Pat. No. 4,820,834. Certain CCK antagonists are useful anxiolytic agents and can be used in the treatment of panic and anxiety disorders.

CCK has been reported to evoke the release of stress hormones such as adrenocorticotrophic hormone, β-endorphin, vasopressin and oxytocin, CCK may function as a mediator of responses to stress and as part of the arousal system. CCK-A receptors are now known to be present in a number of areas of the CNS and may be involved in modulating all of the above.

CCK may be involved in the regulation of stress and its relationship with drug abuse e.g. alleviation of the benzodiazepine withdrawal syndrome (Singh et. al., 1992, *Br. J. Pharmacol.,* 105, 8–10) and neuroadaptive processes.

Since CCK and gastrin also have trophic effects on certain tumours [K. Okyama, *Hokkaido J. Med Sci.,* 206–216 (1985)], antagonists of CCK and gastrin are useful in treating these tumours [see, R. D. Beauchamp et al., *Ann. Surg.,* 202, 203 (1985)].

In the light of discussion in C. Xu et al., *Peptides,* 8, 1987, 769–772, CCK antagonists may also be effective in neuroprotection.

CCK receptor antagonists have been found to inhibit the contractile effects of CCK on iris sphincter and ciliary muscles of monkey and human eyes (Eur. J. Pharmacol., 211(2), 183–187; A. Bill et al., Acta Physiol. Scand., 138, 479–485 [1990]), thus having utility in inducing miosis for therapeutic purposes.

A class of benzodiazepine antagonist compounds has been reported which binds selectively to brain CCK (CCK-B and CCK-A) and gastrin receptors [see M. Bock et al.,*J. Med Chem.,* 32, 13–16 (1989)].

European patent application no. 0 167 919 discloses benzodiazepine CCK and gastrin antagonists substituted in the 3-position by, inter alia, a phenyl urea and in the 5-position by inter alia, pyridine. There is no disclosure of the 5-substituents of the compounds of the present invention.

The present invention provides benzodiazepine compounds of formula (I):

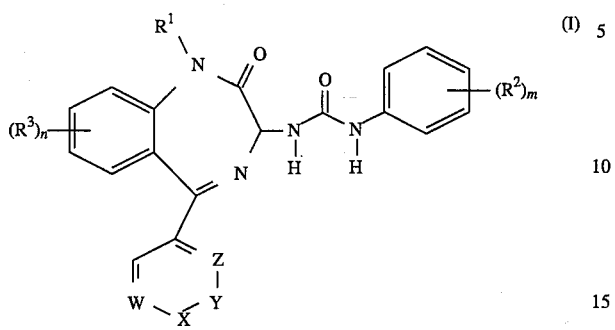

wherein:
- each of W and Z represents a nitrogen atom or a group CH;
- one of X and Y represents a carbonyl group and the other represents a group NH, with the proviso that the system W-X-Y-Z contains no nitrogen-nitrogen bonds;
- $R^1$ represents H, $C_{1-6}$alkyl, $C_{3-7}$cycloalkyl, cyclopropylmethyl, $(CH_2)_q$-imidazolyl, $(CH_2)_q$triazole, $(CH_2)_q$tetrazole (where q is 1, 2 or 3), $CH_2CO_2R^5$ (where $R^5$ is $C_{1-4}$alkyl) or $CH_2CONR^6R^7$ (where $R^6$ and $R^7$ each independently represents H or $C_{1-4}$alkyl, or $R^6$ and $R^7$ together form a chain $(CH_2)_p$ where p is 4 or 5);
- $R^2$ represents $C_{1-6}$alkyl, halo, $(CH_2)_r$-tetrazolyl, optionally substituted in the tetrazolyl ring by $C_{1-4}$alkyl, $(CH_2)_r$-triazolyl, $(CH_2)_r$-imidazolyl, $CONR^6R^7$, $SO(C_{1-6}$alkyl$)$, $SO_2(C_{1-6}$alkyl$)$, $CONHSO_2R^8$, $SO_2NHCOR^8$ (where $R^8$ is $C_{1-6}$alkyl, optionally substituted aryl, 2,2-difluorocyclopropane or trifluoromethyl), $SONHR^9$ (where $R^9$ is a nitrogen containing heterocycle), cyano, $B(OH)_2$ or $(CH_2)_rCO_2H$, where r is zero, 1 or 2;
- $R^3$ represents $C_{1-6}$alkyl or halo;
- m is 0, 1 or 2;
- n is 0, 1, 2 or 3;

and salts or prodrugs thereof.

It will be appreciated that formula (I) is intended to embrace all possible isomers, including optical isomers, and mixtures thereof, including racemates, and tautomers.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bungaard, Elsevier, 1985.

As used herein, alkyl means linear or branched chain alkyl. Examples of suitable alkyl groups include methyl, ethyl, isopropyl and isobutyl groups.

When $R^1$ represents cycloalkyl, examples include cyclopropyl, cyclopentyl and cyclohexyl groups, preferably, cyclopropyl.

Halo includes fluoro, chloro and bromo. Preferably halo will be fluoro or chloro.

Suitable examples of the substituent

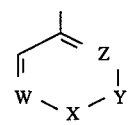

include:

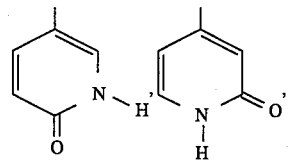

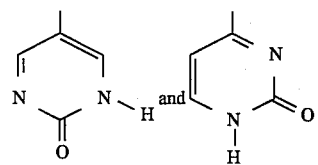

Preferably

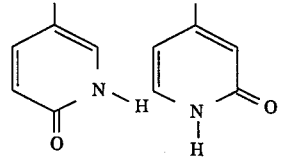

In one group of compounds of formula (I), $R^1$ represents $C_{1-6}$alkyl, $C_{3-7}$cycloalkyl, cyclopropylmethyl, $(CH_2)_q$-imidazolyl (where q is 1 or 2), $CH_2CO_2R^5$ or $CH_2CONR^6R^7$ (where $R^5$, $R^6$ and $R^7$ are as previously defined);

$R^2$ represents $C_{1-6}$alkyl, halo, $(CH_2)_r$-tetrazolyl, $(CH_2)_r$-imidazolyl, $CONHSO_2R^8$, $SO_2NHCOR^8$ (where $R^8$ is $C_{1-4}$alkyl, optionally substituted aryl or trifluoromethyl), or $(CH_2)_rCO_2H$ (where r is zero, 1 or 2); and m and n each represent 0 or 1.

Preferably $R^1$ is $C_{1-6}$alkyl, such as $C_{1-4}$alkyl, more preferably methyl or iso-butyl.

When one substituent $R^2$ is present, it will preferably be located at the 3- or 4-position of the phenyl ring, more preferably the 3-position. When two substituents $R^2$ are present, they will preferably be located at the 3- and 4-positions.

Suitable values for $R^8$ include methyl, ethyl, i-propyl, t-butyl, phenyl and trifluoromethyl.

When $R^8$ is optionally substituted aryl, this will preferably be optionally substituted phenyl. Suitable substituents include $C_{1-4}$alkyl, $C_{1-4}$alkoxy, halo and trifluoromethyl. Preferred are compounds wherein $R^8$ is unsubstituted aryl or aryl substituted by $C_{1-6}$alkyl, for example phenyl substituted by $C_{1-6}$alkyl, such as methyl, in the ortho position.

When $R^8$ is $C_{1-6}$alkyl, it will preferably represent $C_{1-4}$alkyl. Particularly preferred are methyl and isopropyl.

When $R^2$ is $SO_2NHR^9$, suitable values of $R^9$ include, for example, thiazole, thiadiazole and pyrazine.

Preferably $R^2$ is tetrazolyl, methyl, $CONHSO_2R^8$, $SO_2NHCOR^8$ or COOH, more preferably 5-tetrazolyl.

Preferably m is 1.
Preferably n is zero.
Preferably q is 1.
Preferably r is zero.

A particluar sub-class of compounds according to the invention is represented by formula (Ia):

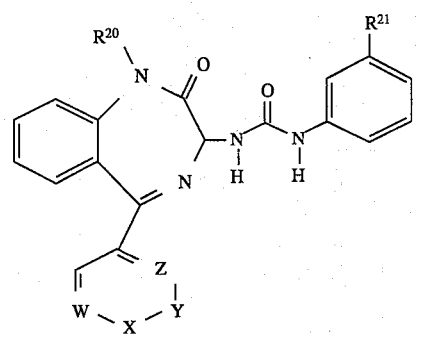

wherein:

W, X, Y and Z are as defined for formula (I), above;

$R^{20}$ is $C_{1-4}$alkyl, preferably iso-butyl; and $R^{21}$ is $C_{1-4}$alkyl, tetrazolyl, $CONHSO_2R^8$ or $SO_2NHCOR^8$, where $R^8$ is as defined for formula (I), preferably tetrazolyl; and salts and prodrugs thereof.

Preferred compounds according to formula (Ia) are those wherein W and Z both represent CH.

Preferably the salts of the compounds of formula (I) are pharmaceutically acceptable, but non-pharmaceutically acceptable salts may be used for the preparation of pharmaceutically acceptable salts.

The pharmaceutically acceptable salts of the compounds of formula (I) include the conventional non-toxic salts or the quaternary ammonium salts of the compounds from formula (I) formed, e.g., from non-toxic inorganic or organic salts. For example, such conventional non-toxic salts include those derived from inorganic acids such as hydrochloric, hydrobromic, sulphuric, sulphamic, phosphoric, nitric and the like; and the salts prepared from organic acids such as acetic, propionic, succinic, glycolic, steric, lactic, malic, tartaric, citric, ascorbic, palmoic, maleic, hydroxymaleic, phenylacetic, glutamic, benzoic, salicylic, sulphanilic, 2-acetoxy benzoic, fumaric, toluenesulphonic, methanesulphonic, ethane disulphonic, oxalic and isothionic.

The salts of the present invention can be synthesized from the compound of formula (I) which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

For example, an acid of formula (I) may be reacted with an appropriate amount of a base, such as an alkali or alkaline earth metal hydroxide e.g. sodium, potassium, lithium, calcium, or magnesium, or an organic base such as an amine, e.g. dibenzylethylenediamine, trimethylamine, piperidine, pyrrolidine, benzylamine, and the like, or a quaternary ammonium hydroxide such as tetramethylammonium hydroxide.

The present invention also encompasses a pharmaceutical composition comprising a compound of formula (I), or a salt or prodrug thereof and a pharmaceutically acceptable carrier or diluent.

The compounds of formula (I) and their salts and prodrugs, may be administered to animals, preferably to mammals, and most especially to a human subject either alone or, preferably, in combination with pharmaceutically acceptable carriers or diluents, optionally with known adjuvants, such as alum, in a pharmaceutical compostion, according to standard pharmaceutical practice. The compounds can be administered orally, parenterally, including by intravenous, intramuscular, intraperitoneal or subcutaneous administration, or topically.

For oral use of an antagonist of CCK, according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavouring agents may be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

For topical administration, a compound of formula (I) may be formulated as, for example, a suspension, lotion, cream or ointment.

For topical administration, pharmaceutically acceptable carriers are, for example, water, mixtures of water and water-miscible solvents such as lower alkanols or arylalkanols, vegetable oils, polyalkylene glycols, petroleum based jelly, ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like.

The compounds of formula (I) antagonise CCK and/or gastrin and are useful for the treatment and prevention of disorders including central nervous system disorders wherein CCK and/or gastrin may be involved. Examples of such disease states include gastrointestinal diseases, including gastrointestinal ulcers, such as peptic and duodenal ulcers, irritable bowel syndrome, gastroesophagenal reflux disease or excess pancreatic or gastrin secretion, acute pancreatitis, or motility disorders; central nervous system disorders, including central nervous system disorders caused by CCK interaction with dopamine, serotonin and other monoamine neurotransmitters, such as neuroleptic disorders, tardive dyskinesia, Parkinson's disease, psychosis or Gilles de la Tourette syndrome; depression; schizophrenia; disorders of appetite regulatory systems; Zollinger-Ellison syndrome, antral and cell hyperplasia, or pain.

The compounds of formula (I) are particularly useful in the treatment or prevention of neurological disorders involving anxiety disorders and panic disorders, wherein CCK and/or gastrin is involved. Examples of such disorders include panic disorders, anxiety disorders, panic syndrome, anticipatory anxiety, phobic anxiety, panic anxiety, chronic anxiety and endogenous anxiety.

The compounds of formula (I) are also useful for directly inducing analgesia, opiate or non-opiate mediated, as well as anesthesia or loss of the sensation of pain.

The compounds of formula (I) may further be useful for preventing or treating the withdrawal response produced by chronic treatment or abuse of drugs or alcohol. Such drugs include, but are not limited to benzodiazepines, cocaine, alcohol and nicotine.

The compounds of formula (I) may further by useful in the treatment of stress and its relationship with drug abuse.

The compounds of formula (I) may further be useful in the treatment of oncologic disorders wherein CCK may be involved. Examples of such oncologic disorders include small cell adenocarcinomas and primary tumours of the central nervous system glial and neuronal cells. Examples of such adenocarcinomas and tumours include, but are not limited to, tumours of the lower oesophagus, stomach, intestine, colon and lung, including small cell lung carcinoma.

The compounds of formula (I) may also be useful as neuroprotective agents, for example, in the treatment and/or prevention of neurodegenerative disorders arising as a consequence of such pathological conditions as stroke, hypoglycaemia, cerebral palsy, transient cerebral ischaemic attack, cerebral ischaemia during cardiac pulmonary surgery or cardiac arrest, perinatal asphyxia, epilepsy, Huntington's chorea, Alzheimer's disease, Amyotrophic Lateral Sclerosis, Parkinson's disease, Olivo-ponto-cerebellar atrophy, anoxia such as from drowning, spinal cord and head injury, and poisoning by neurotoxins, including environmental neurotoxins.

The compounds of formula (I) may further be used to induce miosis for therapeutic purposes after certain types of examination and intraocular surgery. An example of intraocular surgery would include cateract surgery with implantation of an artificial lens. The CCK antagonist compounds of this invention can be used to prevent miosis occuring in association with iritis, ureitis and trauma.

The present invention therefore provides a compound of formula (I) or a salt or prodrug thereof for use in the preparation of a medicament.

The present invention also provides a compound of formula (I) for use in therapy.

In a further or alternative embodiment the present invention provides a method for the treatment or prevention of a physiological disorder involving CCK and/or gastrin which method comprises administration to a patient in need thereof of a CCK and/or gastrin antagonising amount of a compound of formula (I).

When a compound according to formula (I) is used as an antagonist of CCK or gastrin in a human subject, the daily dosage will normally be determined by the prescibing physician with the dosage generally varying according to the age, weight, and response of the individual patient, as well as the severity of the patient's symptoms. However, in most instances, an effective daily dosage wll be in the range from about 0.005 mg/kg to about 100 mg/kg of body weight, and preferably, of from 0.05 mg/kg to about 50 mg/kg, such as from about 0.5 mg/kg to about 20 mg/kg of body weight, administered in single or divided doses. In some cases, however, it may be necessary to use dosages outside these limits. For example, animal experiments have indicated that doses as low as 1 ng may be effective.

In effective treatment of panic syndrome, panic disorder, anxiety disorder and the like, preferably about 0.05 mg/kg to about 0.5 mg/kg of CCK antagonist may be administered orally (p.o.), administered in single or divided doses per day (b.i.d.). Other routes of administration are also suitable.

For directly inducing analgesia, anaesthesia or loss of pain sensation, the effective dosage preferably ranges from about 100 ng/kg to about 1 mg/kg by intravenous administration. Oral administration is an alternative route, as well as others.

In the treatment or irritable bowel syndrome, preferably about 0.1 to 10 mg/kg of CCK antagonist is administered orally (p.o.), administered in single or divided doses per day (b.i.d.). Other routes of administration are also suitable.

The use of a gastrin antagonist as a tumour palliative for gastrointestinal neoplasma with gastrin receptors, as a modulator of central nervous activity, treatment of Zollinger-Ellison syndrome, or in the treatment of peptic ulcer disease, an effective dosage of preferably about 0.1 to about 10 mg/kg administered one-to-four times daily is indicated.

For use as neuroprotective agents the effective dosage preferably ranges from about 0.5 mg/kg to about 20 mg/kg.

Because these compounds antagonise the function of CCK in animals, they may also be used as feed additives to increase the food intake of animals in daily dosage of preferably about 0.05 mg/kg to about 50 mg/kg of body weight.

The compounds of formula (I) may be prepared from intermediates of formula (II)

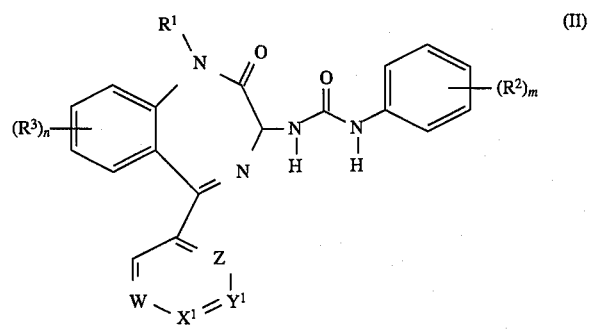

wherein $R^1$, $R^2$, $R^3$, m, n, W and Z are as defined for formula (I) above, and one of $X^1$ and $Y^1$ represents a group C—$OR^{19}$ (where $R^{19}$ is $C_{1-4}$alkyl) and the other represents N with the proviso that the system W-$X^1$-$Y^1$-Z contains no nitrogen-nitrogen bonds, by treatment with a suitable acid, such as a Lewis acid, for example boron tribromide.

The reaction is conveniently effected in a suitable organic solvent, such as a halogenated hydrocarbon, for example, dichloroethane.

Intermediates of formula (II) may be prepared from compounds of formula (III):

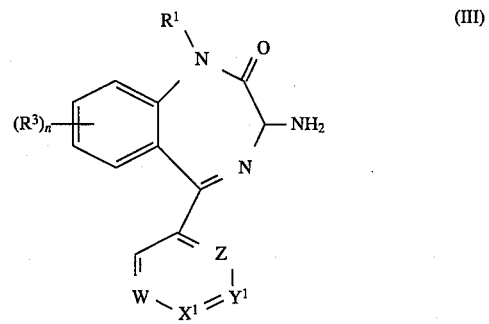

wherein $R^1$, $R^3$, n, W and Z are as defined for formula (I) above, $X^1$ and $Y^1$ are as defined for formula (II) above, by reaction with an isocyanate of formula (IV):

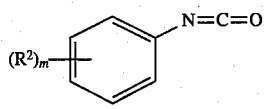

wherein $R^2$ and m are as defined for formula (I).

The reaction is preferably conducted in a suitable organic solvent, such as an ether, for example, tetrahydrofuran, at room temperature.

The isocyanate of formula (IV) may be generated in situ from the corresponding amine by treatment with triphosgene in the presence of a suitable base, such as triethylamine.

Intermediates of formula (III) may be prepared from compounds of formula (V)

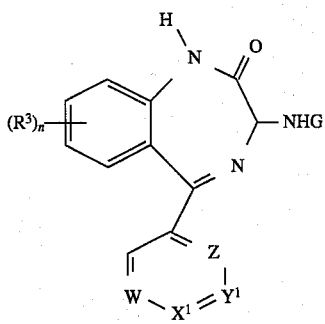

wherein W, Z, n and $R^3$ are as defined for formula (I), $X^1$ and $Y^1$ are as defined for formula (II) and G is a protecting group; by reaction with a reagent suitable to introduce the group $R^1$, for example a halide of formula $R^1$Hal where Hal represents halo such as bromo or iodo, followed by deprotection.

The reaction is carried out in the presence of a base, such as an alkali metal hydride or an alkaline earth metal carbonate, for example sodium hydride or caesium carbonate.

Compounds of formula (V) may be prepared from compounds of formula (VI)

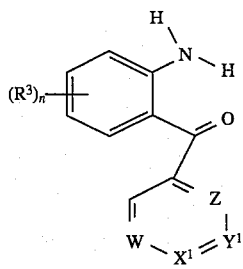

wherein W, Z, n and $R^3$ are as defined for formula (I), and $X^1$ and $Y^1$ are as defined for formula (II) by a reaction sequence comprising:

(i) reaction with a compound of formula (VII)

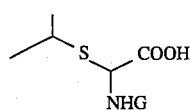

wherein G is as defined above, in the presence of a base, such as a tertiary amine, for example triethylamine or N-methyl morpholine, and a coupling reagent. Any of the coupling reagents commonly used in peptide synthesis are suitable, for example, 1,3-dicyclohexylcarbodiimide (DCC) or isobutyl chloroformate.

(ii) Treatment with gaseous ammonia, preferably in the presence of a mercury containing catalyst, such as mercury(II) chloride. The reaction is conveniently effected in a suitable organic solvent, such as an ether, for example, tetrahydrofuran.

(iii) Treatment with an organic acid, for example acetic or propionic acid, optionally in the presence of an ammonium salt, for example ammonium acetate.

Compounds of formula (VI) may be prepared from the corresponding nitro compounds of formula (VIII):

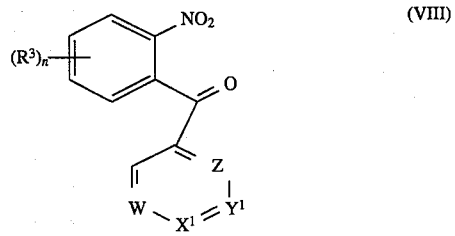

wherein $R^3$, n, W and Z are as defined for formula (I) and $X^1$ and $Y^1$ are as defined for formula (II), by reduction using, for example, hydrogen in the presence of a noble metal catalyst, such as palladium, which may by supported, for example, on carbon.

Conveniently the reaction will be conducted in a suitable solvent, such as an alcohol, for example, ethanol or methanol.

Compounds of formula (VIII) may be prepared from intermediates of formula (IX):

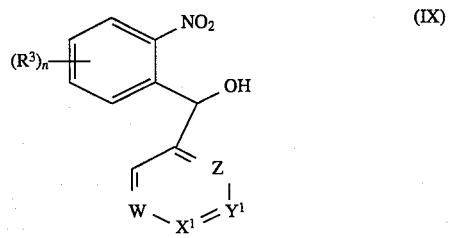

wherein $R^3$, n, W and Z are as defined for formula (I) and $X^1$ and $Y^1$ are as defined for formula (II), by oxidation. Suitable oxidising agents include, for example, pyridine dichromate, or oxalyl chloride and dimethyl sulphoxide, followed by triethylamine (Swern oxidation).

Conveniently the reaction will be effected in a suitable organic solvent such as, for example, dimethylformamide or, if using Swern conditions, dichloromethane. When Swern conditions are used, the reaction is conducted at low temperature, for example, at about −75° C.

Intermediates for formula (IX) may be prepared from compounds of formula (X):

wherein W and Z are as defined for formula (I), $X^1$ and $Y^1$ are as defined for formula (II), and Hal represents halo, such as chloro, bromo or iodo, by abstraction of $Hal^+$ to form an anion using a suitable base, for example, n-butylithuim, and reaction of the anion with a compound of formula (XI):

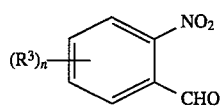

wherein $R^3$ and n are as defined above; or by direct metallation using a suitable metallating reagent, for example, lithium diisopropylamide, and reaction with a compound of formula (XI).

The reaction is conveniently effected in an anhydrous organic solvent, such as an ether, for example tetrahydrofuran at low temperature, such as from about −100° to about −60° C.

Compounds of formulae (X) and (XI) are commercially available or can be prepared by known methods.

Intermediates of formulae (II), (III), (V), (VI), (VIII) and (IX) are novel compounds and form a further aspect of the present invention.

Therefore the present invention further provides intermediates of formulae (A) and (B):

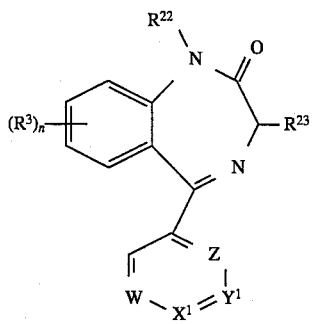

wherein $R^3$, n, W, X', Y' and Z are as above defined;

$R^{22}$ represents H or $R^1$ as above defined.

$R^{23}$ represents optionally protected amino or a group

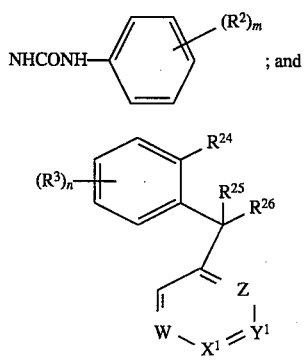

wherein $R^3$, n, W, X', Y' and Z are as above defined;

$R^{24}$ represents $NH_2$ or $NO_2$;

$R^{25}$ represents H and $R^{26}$ represents hydroxy, or $R^{25}$ and $R^{26}$ together represent =O.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-L-tartaric acid and/or (+)-di-p-toluoyl-D-tartaric acid followed by fractional crystallization and regeneration of the free base. The novel compounds may also be resolved by formation of diastereomeric esters or amides, followed by chromatographic separation and removal of the chiral auxiliary. Alternatively, enantiomers of the novel compounds may be separated by HPLC using a chiral column.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene, *Protective Groups in Organic Synthesis*, John Wiley & Sons, 1981. The protecting groups may be removed at a convenient subsequent stage using methods known from the art.

The following examples are provided to assist in a further understanding of the invention. Particular materials employed, species and conditions are intended to be further illustrative of the invention and not limitative of the scope thereof.

EXAMPLE 1

N-[3(R,S)-2,3-Dihydro-1-(2-methylpropyl)-2-oxo-5-(6-oxo-1,6-dihydropyridin-3-yl)-1H-1,4-benzodiazepin-3-yl]-N'-[3-(tetrazol-5-yl)phenyl]urea Step 1: 5-(3-Nitrophenyl)tetrazole To a solution of 3-cyanonitrobenzene (20 g) in 1-methyl-2-pyrrolidinone (200 ml) was added triethylamine hydrochloride (27.9 g) followed by sodium azide (26.4 g). The mixture was heated at 160° C. for 1.5 hours, then cooled to ambient temperature, poured into ice water (1000 ml) and acidified using 5M hydrochloric acid. The solid which precipitated from the mixture was filtered, washed with water and dried under vacuum at 50° C. to afford the title tetrazole (22.1 g) as a beige powder. mp 154°–156° C. $^1$H NMR (360 MHz, CDCl$_3$) δ 7.59 (1H, dd, J=8 Hz), 8.19 (1H, d, J=8 Hz), 8.36 (1H, d, J=8 Hz), 8.86 (1H, s).

Step 2: 5-(3-Aminophenyl)tetrazole hydrochloride

To a solution of 5-(3-nitrophenyl)tetrazole (22 g) in ethanol (500 ml) was added 10% palladium on carbon (1.5 g, 7% (w/w)) in hydrochloric acid (23 ml of a 5M solution). The mixture was hydrogenated at 40 psi for 10 minutes then the catalyst filtered off and washed with water. The solvents were evaporated in vacuo and the brown solid azeotroped with toluene (4×100 ml). The resulting solid was triturated with hot ethanol to give 5-(3-aminophenyl)tetrazole hydrochloride (16.3 g, 71%) as a beige powder. mp 203°–205° C. $^1$H NMR (360 MHz, D$_2$O) δ 7.63 (1H, d, J=8 Hz), 7.75 (1H, dd, J=8 Hz), 8.00 (2H, m).

Step 3: (2-Nitrophenyl)-(6-methoxypyridin-3-yl)methanol n-Butyllithium (6.7 ml of a 1.6M hexane solution) was added dropwise to a stirred, cooled (−100° C.) solution of 5-bromo-2-methoxypyridine (2.0 g, *Eur. J. Med. Chem.* 1977, 12, 531) in anhydrous tetrahydrofuran (60 ml), under a nitrogen atmosphere. After 20 minutes a solution of 2-nitrobenzaldehyde (1.61 g) in anhydrous tetrahydrofuran (30 ml) was added dropwise and the reaction mixture was stirred whilst maintaining the temperature between −90° and −100° C. for 2 hours. The reaction mixture was warmed to −85° C. then quenched with saturated aqueous ammonium chloride solution then allowed to warm to room temperature. The organic layer was separated and the aqueous extracted with ethyl acetate (3× 100 ml). The combined organics were dried (magnesium sulphate) then evaporated to give a gum which was purified by column chromatography on silica using ethyl acetate/petroleum ether (60–80) (1:4) to afford an oil which solidified to give a low melting solid on standing (1.42 g). $R_f$=0.30 in 33% ethyl acetate/petroleum ether (60–80) on silica plates; $^1$H NMR (360 MHz, CDCl$_3$) δ 2.60 (1H, broad s), 3.91 (3H, s), 6.43 (1H, s), 6.70 (1H, d, J=9 Hz), 7.48 (1H, dd, J=1 and 8 Hz), 7.53 (1H, dd, J=3 and 9 Hz), 7.67 (1H, dd, J=1 and 8 Hz), 7.83 (1H, d, J= 8 Hz), 7.96 (1H, dd, J=1 and 8 Hz), 8.11 (1H, d, J=3 Hz); MS, m/z 261 for (M+H)$^+$; IR (KBr) 3300 cm$^{-1}$ (v. broad).

Step 4:
(2-Nitrophenyl)-(6-methoxypyridin-3-yl)methanone

Pyridinium dichromate (18.7 g) was added to a stirred, cooled (0° C.) solution of (2-nitrophenyl)-(6-methoxypyridin-3-yl)methanol (2.0 g) in dimethylformamide (60 ml). After 2 hours at 0° C. water (100 ml) and ethyl acetate (50 ml) were added and the mixture allowed to warm to room temperature. The organic layer was separated and the aqueous extracted with ethyl acetate (3×100 ml). The combined organics were washed with water (2×100 ml) then brine (100 ml), dried (magnesium sulphate) then evaporated to dryness to give the title compound as a solid (1.90 g). mp 94°–95° C. $R_f$=0.35 in 33% ethyl acetate/petroleum ether (60–80) on silica plates; $^1$H NMR (360 MHz, CDCl$_3$) δ 3.97 (3H, s), 6.63 (1H, d, J=9 Hz), 7.47 (1H, dd, J=1 and 8 Hz), 7.70 (1H, dd, J=8 Hz), 7.78 (1H, dd, J= 8 Hz), 8.12 (1H, dd, J=3 and 9 Hz), 8.25 (1H, dd, J=1 and 8 Hz), 8.36 (1H, d, J=3 Hz); MS, m/z 258 for M$^+$.

Step 5:
(2-Aminophenyl)-(6-methoxypyridin-3-yl)methanone

10% Palladium on carbon (1 g) was added to a solution of (2-nitrophenyl)-(6-methoxypyridin-3-yl)methanone (3.6 g) in ethanol (100 ml) and the mixture was hydrogenated at 10 psi (0.7×10$^5$ N.m$^{-2}$) for 30 minutes. The reaction mixture was filtered then evaporated to dryness. The residue was purified by column chromatography on silica using ethyl acetate/petroleum ether (60–80) (1:4) to afford the title compound as a yellow solid (2.78 g). mp 60°–62° C. $R_f$=0.50 in 33% ethyl acetate/petroleum ether (60–80) on silica plates; $^1$H NMR (360 MHz, CDCl$_3$) δ 4.01 (3H, s), 6.64 (1H, ddd, J=1.5 and 8 Hz), 6.74 (1H, d, J=8 Hz), 6.81 (1H, d, J=9 Hz), 7.29 (1H, ddd, J=1.5 and 8 Hz), 7.46 (1H, dd, J=1.5 and 8 Hz), 7.93 (1H, dd, J=3 and 9 Hz), 8.48 (1H, d, J= 3 Hz); MS, m/z 228 for M$^+$; IR (KBr) 1620 and 1600 cm$^{-1}$.

Step 6:
1,3-Dihydro-3(R,S)-(benzyloxycarbonylamino)-5-(6-methoxypyridin-3-yl)-2H-1,4-benzodiazepin-2-one To a stirred, cooled (0° C.) solution of α-(isopropylthio)-N$^α$-(benzyloxycarbonyl)glycine (3.91 g) in anhydrous dichloromethane (100 ml), under a nitrogen atmosphere, was added dropwise a solution of N-methylmorpholine (1.52 ml) in anhydrous dichloromethane (10 ml) followed by a solution of isobutylchloroformate (1.79 ml) in anhydrous dichloromethane (10 ml). The reaction mixture was stirred at 0° C. for 30 minutes then heated to reflux. (2-Aminophenyl)-(6-methoxypyridin-3-yl)methanone (3.0 g) in anhydrous dichloromethane (30 ml) was added dropwise then the mixture was heated at reflux for 30 minutes then stirred at room temperature for 18 hours. The reaction mixture was washed with 10% aqueous citric acid (2× 25 ml), then with saturated aqueous sodium bicarbonate (2× 25 ml). The organic layer was separated, dried (sodium sulphate) then evaporated to dryness and the residue was purified by column chromatography on silica using 10% ethyl acetate/petroleum ether (60–80) –40% ethyl acetate/petroleum ether (60–80) to afford the (isopropylthio)glycinamide (1.99 g). This product was dissolved in anhydrous tetrahydrofuran (100 ml), cooled to 0° C. then saturated with ammonia gas. Mercuric chloride (1.15 g) was added and the reaction mixture stirred at 0° C. for 4 hours whilst maintaining the flow of ammonia. A further quantity of mercuric chloride (0.70 g) was added during this period. The reaction mixture was filtered, then evaporated to give a semi-solid which was dissolved in glacial acetic acid (50 ml) and treated with ammonium acetate (1.86 g). The reaction mixture was stirred at room temperature overnight, evaporated to dryness, basified using 4M sodium hydroxide solution then extracted with ethyl acetate (4×100 ml). The combined organics were dried (sodium sulphate) and evaporated to dryness. The residue was purified by column chromatography on silica using 5%–30% diethyl ether/dichloromethane to afford the title benzodiazepine as a colourless solid (1.005 g). mp 183°–184° C. $R_f$=0.20 in 10% diethyl ether/dichloromethane on silica plates; $^1$H NMR (360 MHz, DMSO-d$_6$) δ 3.90 (3H, s), 5.01 (1H, m), 5.07 (2H, s), 6.88–8.40 (12H, m); MS, FAB$^-$, m/z 415 for (M-H)$^-$. (Found: C, 65.28; H, 4.82; N, 13.06. C$_{23}$H$_{20}$N$_4$O$_4$.0.4H$_2$O requires C, 65.21; H, 4.95; N, 13.23%).

Step 7:
1,3-dihydro-3(R,S)-(benzyoxycarbonylamino)-1-(2methylpropyl)-
5-(6-methoxypyrdin-3-yl)-2H-1,4-benzodiazepin-2-one Sodium hydride (92 mg of a 55% oil dispersion) was added to a stirred, cooled (2° C.) solution of 1,3-dihydro-3(R,S)-(benzyloxycarbonylamino)- 5-(6-methoxypyridin-3-yl)-2H-1,4-benzodiazepin- 2-one (800 mg) in anhydrous dimethylformamide (50 ml), under a nitrogen atmosphere. After 20 minutes 1-iodo-2-methylpropane (0.24 ml) was added then the cooling bath was removed. The reaction mixture was stirred at room temperature for 18 hours then evaporated to dryness. The residue was partitioned between dichloromethane and water. The organic layer was separated and the aqueous re-extracted with dichloromethane. The combined organics were washed with brine, dried (sodium sulphate) then evaporated. The residue obtained was purified by column chromatography on silica using 2.5%–15% diethyl ether/dichloromethane to give the title compound (500 mg). mp 70°–75° C. $R_f$=0.60 in 20% diethyl ether/dichloromethane on silica plates; $^1$H NMR (360 MHz, DMSO-d$_6$) δ 0.42 (3H, d, J=6.5 Hz), 0.70 (3H, d, J=6.5 Hz), 1.52–1.68 (1H, m), 3.62 (1H, dd, J=5 and 13 Hz), 3.91 (3H, s), 4.15 (1H, dd, J=9 and 13 Hz), 5.05 (2H, s), 5.10 (1H, d, J=7 Hz), 6.93 (1H, d, J=8 Hz), 7.28–7.47 and 7.72–7.81 (9H, m), 7.91 (1H, dd, J=2 and 8 Hz), 8.20 (1H, d, J=2 Hz), 8.41 (1H, d, J=7 Hz); MS, FAB$^+$, m/z 473 for (M+H)$^+$. (Found: C, 68.24; H, 5.97; N, 1.62. C$_{27}$H$_{28}$N$_4$O$_4$.0.2H$_2$O requires C, 68.11; H, 6.01; N, 1.77%).

Step 8:
N-[3(R,S)-2,3,Dihydro-1-(2-methylpropyl)-2-oxo-5-(6-methoxypyridin-3-yl)-1H-1,4-benzodiazepin-3-yl]-N'-[3-(tetrazol-5-yl)]phenyl]urea 10% Palladium on carbon (120 mg) was added to a stirred solution of 1,3-dihydro-3(R,S)-(benxyloxycarbonylamino)-1-(2-methylpropyl)- 5-(6-methoxypyridin-3-yl)-2H-1,4-benzodiazepin- 2-one (390 mg) in methanol/formic acid (95.5:4.5) (70 ml) and the reaction mixture was stirred at room temperature for 6 hours. The reaction mixture was filtered and evaporated to dryness. The residue was partitioned between ethyl acetate and 10% sodium bicarbonate solution. The organic layer was separated and the aqueous re-extracted with ethyl acetate (twice). The combined organics were dried (sodium sulphate) and the solvent evaporated to give the crude amine (310 mg).

5-(3-Aminophenyl)tetrazole hydrochloride (230 mg) in anhydrous tetrahydrofuran (10 ml) was treated with triethylamine (0.36 ml) then cooled (ice-bath). Triphosgene (120 mg) was added, the cooling bath was removed and further triethylamine (0.36 ml) added. After 30 minutes at room temperature a solution of the foregoing amine (310 mg) in anhydrous tetrahydrofuran (10 ml) was added and the reaction mixture was stirred for 1 hour. Ethyl acetate and 20% aqueous acetic acid were added, the organic layer was separated and the aqueous re-extracted with ethyl acetate (three times). The combined organics were washed with brine, dried (sodium sulphate) then the solvent evaporated. The solid obtained was triturated with methanol then purified by column chromatography on silica initially using tetrahydrofuran as eluant then changing to 5% acetic acid/tetrahydrofuran to afford a solid which was triturated with dichloromethane to give the title compound (210 mg). mp 246°–247° C. (dec.). $R_f$=0.68 in 2% acetic acid/tetrahydrofuran on silica plates; $^1$H NMR (360 MHz, DMSO-$d_6$) δ 0.52 (3H, d, J=7 Hz), 0.73 (3H, d, J=7 Hz), 1.58– 1.73 (1H, m), 3.66 (1H, dd, J=5 and 13 Hz), 3.91 (3H, s), 4.18 (1H, dd, J=9 and 13 Hz), 5.27 (1H, d, J=8 Hz), 6.93 (1H, d, J= 9 Hz), 7.36–7.83 (9H, m), 7.94 (1H, dd, J=2 and 9 Hz), 8.20 (1H, s), 9.34 (1H, s). (Found: C, 61.05; H, 4.98; N, 23.20. $C_{27}H_{27}N_9O_3$.0.25$H_2O$ requires C, 61.18; H, 5.23; N, 23.78%).

Step 9:
N-[3(R,S)-2,3-Dihydro-1-(2-methylpropyl)-2-oxo-5-(6-oxo-1,6-dihydropyridin-3-yl)-1H-1,4-benzodiazepin-3-yl]-N'-[3-(tetrazol- 5-yl)phenyl]urea To a stirred, cooled (0° C.) suspension of the foregoing tetrazole (160 mg) in 1,2-dichloroethane (30 ml), under a nitrogen atmosphere, was added 1M boron tribromide in dichloromethane (14 ml) dropwise. The yellow suspension was stirred at 0° C. for 45 minutes then at room temperature for 18 hours. Further boron tribromide (1M, 20 ml ) was added and the mixture stirred for 48 hours. The reaction mixture was cooled (0° C.) then cautiously quenched with methanol. The reaction mixture was evaporated to dryness then the residue was purified by column chromatography on silica using dichloromethane/methanol/acetic acid (94:6:0.6–85:15:0.6) and the resulting product triturated with methanol to give the title compound (80 mg). mp 212° C. $R_f$=0.10 in dichloromethane/methanol/acetic acid (94:6:0.6) on silica plates; $^1$H NMR (360 MHz, DMSO-$d_6$) δ 0.53 (3H, d, J=6.5 Hz), 0.72 (3H, d, J=6.5 Hz), 1.56–1.68 (1H, m), 3.62 (1H, dd, J=5 and 13 Hz), 4.16 (1H, dd, J=9 and 13 Hz), 5.20 (1H, d, J=7 Hz), 6.42 (1H, d, J=10 Hz), 7.30–7.79 (9H, m), 7.80 (1H, dd, J=3 and 10 Hz), 8.18 (1H, s), 9.32 (1H, s), 11.85 (1H, broad s). (Found: C, 55.52; H, 5.14; N, 22.14. $C_{26}H_{25}N_9O_3$.2.5$H_2O$.0.2$CH_3OH$ requires C, 55.89; H, 5.51; N, 22.39%).

EXAMPLE 2
N-[3(R,S)-2,3-Dihydro-1-(2-methylpropyl)-2-oxo-5-(2-oxo-1,2-dihydropyridin-4-yl)-1H-1,4-benzodiazepin-3-yl]-N'-[3-(tetrazol-5-yl)phenyl]urea

Step 1:
(2-Nitrophenyl)-(5-bromo-2-methoxypyridin-4-yl)methanol n-Butyllithium (17.5 ml of a 1.6M hexane solution)in anhydrous tetrahydrofuran (20 ml) was added dropwise to a stirred, cooled (−72° C.) solution of diisopropylamine (3.8 ml) in anhydrous tetrahydrofuran (120 ml) under a nitrogen atmosphere. 5-Bromo-2-methoxypyridine (5.09 g, *Eur. J. Med. Chem.* 1977, 12, 531) in anhydrous tetrahydrofuran (15 ml) was added dropwise followed by a solution of 2-nitrobenzaldehyde (2.96 g) in anhydrous tetrahydrofuran (20 ml) keeping the temperature of the reaction mixture below −70° C. The reaction mixture was stirred for 3 hours at −60° C. to −70° C. then quenched with saturated aqueous ammonium chloride solution. The organic layer was separated, washed with water then dried (magnesium sulphate) and evaporated to dryness. The residue was combined with crude product from another reaction of identical scale then purified by column chromatography on silica using ethyl acetate/petroleum ether (60–80) (1:4) and the solid obtained recrystallised from dichloromethane/petroleum ether (60–80) to afford the title compound (8.69 g). mp 128°–131° C. $R_f$= 0.69 in 20% diethyl ether/dichloromethane on silica plates; $^1$H NMR (360 MHz, CDCl$_3$) δ 3.93 (3H, s), 6.42 (1H, s), 7.00 (1H, s), 7.31 (1H, dd, J=1 and 7 Hz), 7.49 (1H, ddd, J=1 and 7 Hz), 7.58 (1H, ddd, J=1 and 7 Hz), 8.02 (1H, dd, J=1 and 7 Hz), 8.19 (1H, s); IR (KBr) 3600–2800 cm$^{-1}$.

Step 2:
(2-Nitrophenyl)-(5-bromo-2-methoxypyridin-4-yl)methanone

Anhydrous dimethylsulphoxide (1.2 ml) in anhydrous dichloromethane (20 ml) was added dropwise to a stirred, cooled (−75° C.) solution of oxalyl chloride (0.7 ml) in anhydrous dichloromethane (100 ml) under a nitrogen atmosphere. After 5 minutes a solution of (2-nitrophenyl)-(5-bromo-2-methoxypyridin- 4-yl)methanol (2.5 g) in anhydrous dichloromethane (70 ml) was added dropwise keeping the temperature of the reaction mixture below −72° C. After a further 15 minutes triethylamine (5.3 ml) was added dropwise and the reaction mixture stirred at −75° C. for 10 minutes then the cooling bath was removed and the mixture allowed to warm to room temperature. Water (50 ml) was added, the organic layer separated, washed with water then dried (sodium sulphate) and evaporated to dryness. The product was dissolved in dichloromethane, treated with activated charcoal, filtered, evaporated to dryness, then recrystallised from dichloromethane/petroleum ether (60–80) to afford the title compound as a pale yellow solid (2.4 g). mp 128°–131° C. $R_f$=0.9 in 10% diethyl ether/dichloromethane on silica plates; $^1$H NMR (360 MHz, CDCl$_3$) δ 3.91 (3H, s), 6.69 (1H, s), 7.59 (1H, dd, J= 1.5 and 7 Hz), 7.74 (1H, dt, J=1.5 and 7 Hz), 7.79 (1H, ddd, J= 1.5 and 7 Hz), 8.13 (1H, dd, J=1.5 and 7 Hz), 8.38 (1H, s); IR (KBr) 1705 and 1695 cm$^{-1}$.

Step 3:
(2-Aminophenyl)-(2-methoxypyridin-4-yl)methanone

Cyclohexene (21 ml) was added to a stirred mixture of (2-nitrophenyl)-(5-bromo-2-methoxypyridin-4-yl)methanone (2.16 g) in ethanol (210 ml). A water slurry of 10% palladium on carbon (216 mg) was added followed by sodium acetate (524 mg). The suspension was heated to reflux for 4.5 hours then the mixture was cooled, filtered and evaporated to dryness. The residue was partitioned between dichloromethane and water. The organic layer was separated and the aqueous re-extracted with dichloromethane (twice). The combined organics were washed with water, brine, dried (sodium sulphate) then evaporated to dryness to give the title compound as a yellow solid (1.45 g). mp 82°–86° C. $R_f$=0.7 in 5% methanol/dichloromethane on silica plates; $^1$H NMR (360 MHz, CDCl$_3$) δ 3.99 (3H, s), 6.57 (1H, ddd, J=1 and 7 Hz), 6.72 (1H, d, J=7 Hz), 6.86 (1H, s), 7.00 (1H, dd, J=1 and 5 Hz), 7.31 (1H, ddd, J=1 and 7 Hz), 7.37 (1H, dd, J=1 and 7 Hz), 8.26 (1H, d, J=5 Hz), IR (KBr) 3450, 3350, 1640 and 1620 cm$^{-1}$.

Step 4:
1,3-Dihydro-3(R,S)-(benzyloxycarbonylamino)-5-(2-methoxypyridin-4-yl)-2H-1,4-benzodiazepin-2-one The title compound was obtained (3.75 g) from (2-aminophenyl)-(2-methoxypyridin-4-yl)methanone as described in Example 1, Step 6. mp 170°–173° C. (ethyl acetate). $R_f$=0.30 in ethyl acetate/petroleum ether (60–80) (1:1) on silica plates; $^1$H NMR (360 MHz, DMSO-d$_6$) δ 3.87 (3H s), 5.07 (1H, d, J=6.5 Hz), 5.08 (2H, s), 6.76 (1H, s), 7.04 (1H, d, J=5 Hz), 7.22–7.45 and 7.62–7.70 (9H, m), 8.25 (1H, d, J=5 Hz), 8.46 (1H, d, J=6.5 Hz), 10.91 (1H, broad s); MS, FAB$^+$, m/z 417 for (M+H)$^+$. (Found: C, 65.53; H, 4.85; N, 13.27. C$_{23}$H$_{20}$N$_4$O$_4$.0.25H$_2$O requires C, 65.63; H, 4.91; N, 13.31%).

Step 5:
1,3-Dihydro-3(R,S)-(benzyloxycarbonylamino)-1-(2-methylpropyl)-5-(2-methoxypyridin-4-yl)-2H-1,4-benzodiazepin-2-one The title compound was obtained from 1,3-dihydro-3(R,S)-(benzyloxycarbonylamino)-5-(2-methoxypyridin-4-yl)-2H-1,4-benzodiazepin-2-one as described in Example 1, Step 7. mp 70°–75° C. $R_f$=0.60 in 20% diethyl ether/dichloromethane on silica plates; $^1$H NMR (360 MHz, DMSO-d$_6$) δ 0.51 (3H, d, J=6.5 Hz), 0.71 (3H, d, J=6.5 Hz), 1.54–1.67 (1H, m), 3.64 (1H, dd, J=5 and 13 Hz), 3.88 (3H, s), 4.15 (1H, dd, J=5 and 13 Hz), 5.06 (2H, s), 5.14 (1H, d, J=7 Hz), 6.77 (1H, s), 7.10 (1H, d, J=6 Hz), 7.30–7.42 and 7.62–7.82 (9H, m), 8.28 (1H, d, J=6 Hz), 8.51 (1H, d, J=7 Hz); MS, FAB$^+$, m/z 473 for (M+H)$^+$. (Found: C, 67.84; H, 5.97; N, 11.60. C$_{27}$H$_{28}$N$_4$O$_4$.0.3H$_2$O requires C, 67.85; H, 6.03; N, 11.72%).

Step 6:
N-[3(R,S)-2,3-Dihydro-1-(2-methylpropyl)-2-oxo-5-(2-methoxypyridin-4-yl)-1H-1,4-benzodiazepin-3-yl]-N'-[3-(tetrazol-5-yl)phenyl]urea The title compound (270 mg) was obtained from 1,3-dihydro-3(R,S)-(benzyloxycarbonylamino)-1-(2-methylpropyl)-5-(2-methoxypyridin-4-yl)-2H-1,4-benzodiazepin-2-one as described in Example 1, Step 8. mp>180° C. (dec). $R_f$=0.68 in 2% acetic acid/tetrahydrofuran on silica plates; $^1$H NMR (360 MHz, DMSO-d$_6$) δ 0.52 (3H, d, J=7 Hz), 0.74 (3H, d, J=7 Hz), 1.58–1.70 (1H, m), 3.68 (1H, dd, J=5 and 13 Hz), 3.88 (3H, s), 4.19 (1H, dd, J=9 and 13 Hz), 5.81 (1H, d, J=8 Hz), 6.76 (1H, s), 7.12 (1H, d, J=5.4 Hz), 7.38–7.85 (8H, m), 8.19 (1H, s), 8.28 (1H, d, J=5.4 Hz), 9.35 (1H, s). (Found: C, 60.21; H, 5.09; N, 22.88. C$_{27}$H$_{27}$N$_9$O$_3$.0.75H$_2$O requires C, 60.16; H, 5.33; N, 23.38%).

Step 7:
N-[3(R,S)-2,3-Dihydro-1-(2-methylpropyl)-2-oxo-5-(2-oxo-1,2-dihydropyridin-4-yl)-1H-1,4-benzodiazepin-3-yl]-N'-[3-(tetrazol-5-yl)phenyl]urea The title compound (35 mg) was obtained from the foregoing methoxypyridine as described in Example 1, Step 9. mp 250° C. (dec). $R_f$=0.10 in dichloromethane/methanol/acetic acid (94:6:0.6) on silica plates; $^1$H NMR (360 MHz, DMSO-d$_6$) δ 0.54 (3H, d, J=7 Hz), 0.74 (3H, d, J=7 Hz), 1.56–1.70 (1H, m), 3.66 (1H, dd, J=5 and 13 Hz), 4.18 (1H, dd, J=9 and 13H$_z$), 5.27 (1H, d, J=8 Hz), 6.17 (1H, s), 6.44 (1H, d, J=7 Hz), 7.38–7.84 (9H, m), 8.18 (1H, s), 9.34 (1H, s), 11.80 (1H, broad s). (Found: C, 58.79; H, 4.94; N, 23.49. C$_{26}$H$_{25}$N$_9$O$_3$.H$_2$O requires C, 58.97; H, 5.14: N, 23.81%).

EXAMPLE 3A

Tablets containing 1–25 mg of Compound

|  | Amount mg | | |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 3B

Tablets Containing 26–100 mg of Compound

|  | Amount mg | | |
|---|---|---|---|
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 4

Parenteral Injection

|  | Amount mg |
|---|---|
| Compound of formula (I) | 1 to 100 mg |

-continued

| | Amount mg |
|---|---|
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 5

Topical Formulation

| | Amount mg |
|---|---|
| Compound of formula (I) | 1-10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

BIOLOGICAL ACTIVITY

1. CCK Receptor Binding (Pancreas)

CCK-8 sulphated was radiolabelled with $^{125}$I-Bolton Hunter reagent (2000 Ci/mmole). Receptor binding was performed according to Chang and Lotti (Proc. Natl. Acad. Sci. 83, 4923–4926, 1986) with minor modifications.

Male Sprague-Dawley rats (150–200 g) were sacrificed by decapitation. The whole pancreas was dissected free of fat tissue and was homogenized in 25 volumes of ice-cold 10 mM N-2-hydroxyethyl-piperazine-N'-2-ethane sulphonic acid (HEPES) buffer with 0.1% soya bean trypsin inhibitor (pH 7.4 at 25° C.) with a Kinematica Polytron. The homogenates were centrifuged at 47,800 g for 10 min. Pellets were resuspended in 10 volumes of binding assay buffer (20mM (HEPES)), 1 mM ethylene glycol-bis-(β-aminoethylether-N,N' -tetraacetic acid) (EGTA), 5 mM $MgCl_2$, 150 mM NaCl, bacitracin 0.25 mg/ml, soya bean trypsin inhibitor 0.1 mg/ml, and bovine serum albumin 2 mg/ml pH 6.5 at 25° C.) using a Teflon (trademark) homogenizer, 15 strokes at 500 rpm. The homogenate was further diluted in binding assay buffer to give a final concentration of 0.5 mg original wet weight/1 ml buffer. For the binding assay, 50 μl of buffer (for total binding) or unlabelled CCK-8 sulphated to give a final concentration of 1 μM (for nonspecific binding) or the compounds of Formula I (for determination of inhibition of $^{125}$I-CCK-8 binding) and 50 μl of 500 pM $^{125}$I-CCK-8 (i.e. 50 pM final concentration) were added to 400 μl of the membrane suspensions in microfuge tubes. All assays were run in duplicate. The reaction mixtures were incubated at 25° C. for 2 hours and the reaction terminated by rapid filtration (Brandell 24 well cell harvester) over Whatman GF/C filters, washing 3×4 mls with ice-cold 100 Mm NaCl. The radioactivity on the filters was counted with a LKB gamma counter.

2. CCK Receptor Binding (Brain)

CCK-8 sulphated was radiolabelled and the binding was performed according to the description for the pancreas method with minor modifications.

Male Hartley guinea pigs (300–500 g) were sacrificed by decapitation and the cortex was removed and homogenized in 25 mL ice-cold 0.32M sucrose. The homogenates were centrifuged at 1000 g for 10 minutes and the resulting supernatant was recentrifuged at 20,000 g for 20 minutes. The $P_2$ pellet was resuspended in binding assay buffer (20 mM HEPES, 5 mM $MgCl_2$, 0.25 mg/ml bacitracin, 1 mM EGTA pH 6.5 at 25° C.), using a Teflon (trademark) homogenizer (5 strokes at 500 rpm) to give a final concentration of 10 mg original wet weight/1.2 ml buffer. For the binding assay, 50 μl of buffer (for total binding) or unlabelled CCK-8 sulphated to give a final concentration of 1 μM (for nonspecific binding) or the compounds of Formula I (for determination of inhibition of $^{125}$I-CCK-8 binding) and 50 μl of 500 pM $^{125}$I-CCK-8 (i.e. final concentration of 50 pM) were added to 400 μl of the membrane suspensions in microfuge tubes. All assays were run in duplicate. The reaction mixtures were incubated at 25° C. for 2 hours and then the reaction was terminated by rapid filtration (Brandell 24 well cell harvester) on Whatman GF/C filters with 3×5 ml washes of cold 100 mM NaCl. The radioactivity on the filters was counted with a LKB gamma counter.

In Vitro Results

Effects of the Compounds of Formula I on $^{125}$I-CCK-8 receptor binding

The preferred compounds of Formula I are those which produced dose-dependent inhibition of specific $^{125}$I-CCK-8 binding as defined as the difference between total and non-specific (i.e. in the presence of 1 μM CCK) binding.

Drug displacement studies were performed with at least 10 concentrations of compounds of Formula I and the $IC_{50}$ values were determined by regression analysis $IC_{50}$ refers to the concentration of the compound required to inhibit 50% of specific binding of $^{125}$I-CCK-8.

The data in Table I were obtained for compounds of Formula I.

TABLE I

| CCK RECEPTOR BINDING RESULTS $IC_{50}$(nM) | | |
|---|---|---|
| Compound of Ex # | $125_{I-CCK}$ Pancreas | $125_{I-CCK}$ Brain |
| 1 | 2680 | 19.2 |

TABLE I-continued

| CCK RECEPTOR BINDING RESULTS IC$_{50}$(nM) | | |
|---|---|---|
| Compound of Ex # | 125$_{I\text{-}CCK}$ Pancreas | 125$_{I\text{-}CCK}$ Brain |
| 2 | 3380 | 23.0 |

I claim:

1. A compound of formula (I), or a salt or prodrug thereof:

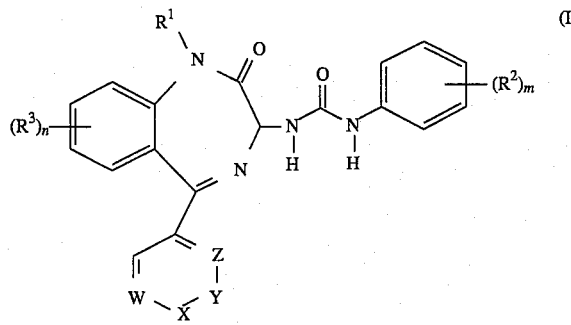

wherein:

each of W and Z represents a nitrogen atom or a group CH;

one of X and Y represents a carbonyl group and the other represents a group NH, with the proviso that the system W-X-Y-Z contains no nitrogen-nitrogen bonds;

$R^1$ represents H, $C_{1-6}$alkyl, $C_{3-7}$cycloalkyl, cyclopropylmethyl, $(CH_2)_q$-imidazolyl, $(CH_2)_q$triazole, $(CH_2)_q$tetrazole (where q is 1, 2 or 3 ), $CH_2CO_2R^5$ (where $R^5$ is $C_{1-4}$alkyl) or $CH_2CONR^6R^7$ (where $R^6$ and $R^7$ each independently represents H or $C_{1-4}$alkyl, or $R^6$ and $R^7$ together form a chain $(CH_2)_p$ where p is 4 or 5);

$R^2$ represents $C_{1-6}$alkyl, halo, $(CH_2)_r$-tetrazolyl, optionally substituted in the tetrazolyl ring by $C_{1-4}$alkyl, $(CH_2)_r$-triazolyl, $(CH_2)_r$-imidazolyl, $CONR^6R^7$, $SO(C_{1-6}$alkyl), $SO_2(C_{1-6}$alkyl), $CONHSO_2R^8$, $SO_2NHCOR^8$ (where $R^8$ is $C_{1-6}$alkyl, optionally substituted aryl, 2,2-difluorocyclopropane or trifluoromethyl), $SONHR^9$ (where $R^9$ is a nitrogen containing heterocycle), cyano, $B(OH)_2$ or $(CH_2)_rCO_2H$, where r is zero, 1 or 2;

$R^3$ represents $C_{1-6}$alkyl or halo;

m is 0, 1 or 2; and n is 0, 1, 2 or 3.

2. A compound as claimed in claim 1 wherein $R^1$ represents $C_{1-6}$alkyl, $C_{3-7}$cycloalkyl, cyclopropylmethyl, $(CH_2)_q$-imidazolyl (where q is 1 or 2), $CH_2CO_2R^5$ or $CH_2CONR^6R^7$ (where $R^5$, $R^6$ and $R^7$ are as previously defined);

$R^2$ represents $C_{1-6}$alkyl, halo, $(CH_2)_r$-tetrazolyl, $(CH_2)_r$-imidazolyl, $CONHSO_2R^8$, $SO_2NHCOR^8$ (where $R^8$ is $C_{1-4}$alkyl, optionally substituted aryl or trifluoromethyl), or $(CH_2)_rCO_2H$ (where r is zero, 1 or 2); and m and n each represent 0 or 1.

3. A compound as claimed in claim 2 wherein the substituent

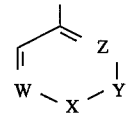

is 6-oxo-1,6-dihydropyridin-3-yl or 2-oxo-1,2-dihydropyridin-4-yl.

4. A compound as claimed in claim 3 wherein $R^1$ is $C_{1-6}$alkyl.

5. A compound as claimed in claim 4 wherein $R^2$ is tetrazolyl, methyl, $CONHSO_2R^8$, $SO_2NHCOR^8$ or COOH.

6. A compound as claimed in claim 1 selected from N-(3(R,S)-2,3-dihydro-1-(2-methylpropyl)-2-oxo-5-(6-oxo-1,6-dihydropyridin-3-yl)-H-1,4-benzodiazepin-3-yl-N'-(3-tetrazol-5-yl)phenyl)urea; N-(3(R,S)-2,3-dihydro-1-(2-methylpropyl)-2-oxo-5-(2-oxo-1,2-dihydropyridin-4-yl)-1H-1,4-benzodiazepin-3-yl-N'-(3-tetrazol-5-yl)phenyl)urea; and salts and prodrugs thereof.

* * * * *